US005648083A

United States Patent [19]
Blieszner et al.

[11] Patent Number: 5,648,083
[45] Date of Patent: Jul. 15, 1997

[54] PERSONAL CARE COMPOSITIONS AND WIPE PRODUCTS CONTAINING THE COMPOSITIONS

[75] Inventors: Kathleen Clare Blieszner; George Endell Deckner, both of Cincinnati, Ohio

[73] Assignee: The Procter & Gamble Company, Cincinnati, Ohio

[21] Appl. No.: 386,973

[22] Filed: Feb. 10, 1995

[51] Int. Cl.[6] .................... A61K 31/74; A01N 25/34
[52] U.S. Cl. .................... 424/402; 424/404; 424/443
[58] Field of Search .................... 424/401, 443, 424/402, 404, 411, 413; 514/855, 865, 938; 604/305

[56] References Cited

U.S. PATENT DOCUMENTS

| | | | |
|---|---|---|---|
| 2,798,053 | 7/1957 | Brown | 260/2.2 |
| 3,915,921 | 10/1975 | Schlatzer, Jr. | 260/17.4 |
| 3,987,184 | 10/1976 | Foelsch | 424/273 |
| 4,370,319 | 1/1983 | Chapin et al. | 424/184 |
| 4,382,960 | 5/1983 | Flom | 424/358 |
| 4,509,949 | 4/1985 | Huang et al. | 586/558 |
| 4,797,310 | 1/1989 | Barby et al. | 428/71 |
| 4,844,891 | 7/1989 | Rosen et al. | 424/76.4 |
| 5,043,155 | 8/1991 | Puchalski et al. | 424/78 |
| 5,059,282 | 10/1991 | Ampulski et al. | 162/111 |
| 5,156,843 | 10/1992 | Leong et al. | 424/411 |
| 5,332,118 | 7/1994 | Muckenfuhs | 221/48 |

FOREIGN PATENT DOCUMENTS

932936  9/1973  Canada .................... 28/53

OTHER PUBLICATIONS

Derwent Abstract No. 72–79526T (Patent N. SU–336019A) Prevention of Dermatits—Using Mixture of Aminobentonite and Polyethylsiloxane, Kharkov Pharmaceutical In, Apr. 21 1972.

Derwent Abstract No. 86–201674 (Patent No. JP61134322A) Contact Dermatitis Preventing Composition—Comprises Animal and Vegetable Oils and Silicone Oil, KAO Corp., Jun. 21, 1986.

Derwent Abstract No. 87–209273 (Patent No. JP62135414A, JP90038567B) Wiping and Cleaning Composition for Skin, esp. for Anus Area—Includes Vegetable Animal and/or Synthetic Oil, Silicone Oil and Lower Alcohol, KAO Corp., Jun. 18, 1987, Aug. 31 1990.

Derwent Abstract No. 87–209274 (Patent No. JP62135415A, JP93058408B) Wiping and Cleaning Agent Composition for Skin—Contains Silicone Oil, Cyclic Di Methyl Silicon and Ethanol and/or Isopropanol, KAO Corp., Jun. 18, 1987, Aug. 26, 1993.

Derwent Abstract No. 89–134276 (Patent No. JP01079108A) New Cleaning Wiping Agent Composition Containing Polyoxyalkylene Modified Organo–Polysiloxane(s), Shiseido Co., Ltd., Mar. 24, 1989.

Derwent Abstract No. 89–136215 (Patent No. JP01083014A) Safe Cleaning–Wiping Agent Composition Having Good Effect—Contains Polyoxyalkylene Modified Organo–Polysiloxane(s), Shiseido Co. Ltd., Mar. 28, 1989.

Derwent Abstract No. 89–353213 (Patent No. JP01265019A) Skin Cleansing Composition—Comprises Aerosol Containing Water Soluble Silicone and Phosphoric Acid Buffer, Sunstar KK, Oct. 23, 1989.

Derwent Abstract No. 92–013559 (Patent No. JP03264520A) Composition for Skin Cleansing by Application to Toilet Ppaper—Contains Vegetable Oil, Animal Oil and/or Synthetic Oil, Silicone Oil, and Buffer to Adjust Skin pH to 3–6, KAO Corp. Nov. 25, 1991.

Derwent Abstract No. 92–060684 (Patent No. JP04005224A) Skin Cleansing Composition for Use in Vaginal, Anal, etc., Areas—Comprises Water–Miscible Solvent and CPD. Giving Ion(s) of Alkaline Earth Metal, Manganese, Zinc, Cobalt or Nickel, KAO Corp., Jan. 9, 1992.

Derwent Abstract No. 92–076737 (Patent No. JP04021625A) Skin Cleaning Wiping composition Especially Effective For Cleaning Anus—Consisting of High Molecular Silicone(s) and Silicone Oil(s) of Specific Viscosity, KAO Corp., Jan. 24, 1992.

Derwent Abstract No. 93–111902 (Patent No. JP05049551A) Wet Tissue For Cleaning Skin—Comprises e.g. Paper Base Impregnated With Liquid Medicinal Agent, Paraffin and Gamma–Linolenic Acid, JEX KK, Mar. 2, 1993.

Dow Corning Corporation, Information About Dow Corning Silicone Fluids, Form No. 22–928E–94, 1994.

Dow Corning Corporation, Shaping Solutions For Personal Care, Form No. 24–414C–93, 1993.

Dept. of Health and Human Services, Federal Register vol. 48, No. 32, Skin Protectant Drug Products for Over–the–counter Human Use; Tentative Final Monograph; Proposed Rule, Feb. 15, 1983, pp. 6820–6833.

Dept. of Health and Human Services, Federal Register vol. 55, No. 119, Skin Protectant Drug Products for Over–the–Counter Human Use; Diaper Rash Products; Proposed Rule, Jun. 20, 1990, pp. 25204–25232.

Primary Examiner—Thurman K. Page
Assistant Examiner—Sharon Howard
Attorney, Agent, or Firm—Bart S. Hersko; E. Kelly Linman; Jacobus C. Rasser

[57] ABSTRACT

Personal care compositions that are especially suitable for personal cleansing of the perineal area and protection against perineal dermatitis are disclosed. Preferred compositions include water, dimethicone, a polymeric emulsifier and optionally a water-soluble polyol, a pH-adjusting agent, an anti-microbial agent, and a chelating agent. Also disclosed are disposable wipe products containing a nonwoven or other substrate impregnated with the composition.

26 Claims, No Drawings

PERSONAL CARE COMPOSITIONS AND WIPE PRODUCTS CONTAINING THE COMPOSITIONS

FIELD OF THE INVENTION

The present invention relates to personal care compositions, more particularly personal cleansing and/or skin treating compositions. The compositions are useful, for example, for perineal cleansing and protection against perineal dermatitis.

BACKGROUND OF THE INVENTION

Perineal dermatitis (including diaper dermatitis) has been defined as contact dermatitis in the perineal area, including the perineum, buttocks, and the perianal, coccyx and upper/inner thigh regions (Brown D. S., Sears M., Perineal Dermatitis: A Conceptual Framework, Ostomy/Wound Management 1993, 39 (7), 20–25). The physical signs of perineal dermatitis may include one or a combination of erythema, swelling, oozing, vesiculation, crusting and scaling, with the possibility of excoriation, thickening and hyperpigmentation over time (Brown).

Perineal dermatitis is believed to be caused by the prolonged contact of the skin with body waste such as urine and feces. Although the exact component(s) of body waste responsible for perineal dermatitis has not been identified, factors that are suspected of causing perineal dermatitis include ammonia, moisture, bacteria, urine pH, and *Candida albicans*. Because these various suspected factors have different properties and require different therapies, one of the most effective methods of treating perineal dermatitis has been the application of a topical protective barrier agent between the skin and the body waste.

Several topically applied barrier agents are or have been commercially available. Exemplary agents are listed, for example, in U.S. Pat. No. 5,043,155 issued to Puchalski et al. on Aug. 27, 1991. Such agents are typically in the form of powders, lotions, creams and ointments and may contain a variety of ingredients. For example, the agents listed in the U.S. Pat. No. 5,043,155 may contain calcium undecylenate, talc, starch, calcium carbonate, petrolatum, cod liver oil, vitamins A and D, lanolin, balsam, silicone, including dimethicone, zinc oxide, bismuth subnitrate, benzalkonium chloride, methylbenzethonium chloride, and protein hydrolysate containing amino acids.

Skin protectant agents, for example, dimethicone, are also disclosed in the Federal Register, Vol. 48, No. 32, Feb. 15, 1983, pages 6820–6833 (proposed rule of the U.S. Dept. of Health and Human Services, Federal Food and Drug Administration). Skin protectant drug products for over-the-counter human use, such as diaper rash products, which may include, for example, dimethicone, are discussed in the Federal Register, Vol. 55, No. 119, Jun. 20, 1990, pages 25204–25232 (proposed rule of the U.S. Dept. of Health & Human Services, Federal Food and Drug Administration).

Known personal cleansing compositions may contain very small amounts of anti-foaming agents, e.g., silicone oils. Such anti-foaming agents are typically employed in amounts of less than about 0.01 weight % of the composition. Such minute amounts do not provide any significant benefits to the skin.

Barrier agents for protection against perineal dermatitis may be applied by sprinkling the agent onto the skin, by massaging the material into the skin with the hands, or via a wiping material. Wiping materials are typically used for cleansing while changing an infant diaper or adult incontinence article. Disposable wipes are pre-moistened, disposable towelettes. The towelette is typically a nonwoven formed of various combinations of cellulosic fibers, synthetic polymeric fibers such as polyester, polypropylene and the like, and binders. The nonwoven is generally moistened with a composition containing water (94% or more) and various combinations of other ingredients including moistening agents or humectants, emollients, surfactants, emulsifiers, anti-microbial agents, skin protectants, pH-adjusting agents, fragrances, powders and the like. Several exemplary ingredients that may be used in disposable baby wipes are disclosed in the above referenced U.S. Pat. No. 5,043,155.

As recognized in U.S. Pat. No. 5,043,155, many wipes have historically required the separate application of a barrier agent. More recently, wipes that are said to cleanse and carry a skin protectant onto the skin have become commercially available. An example of such wipes are Baby Fresh With Ultra Guard® baby wipes. The Baby Fresh® baby wipes are marketed with a patent marking of U.S. Pat. No. 4,904,524 (issued to Yoh on Feb. 27, 1990).

It is desirable that, in addition to providing effective cleansing, the wipe itself leave a substantive, highly protective residue on the skin. In order to provide maximum protection against perineal dermatitis, it is desirable that compositions used in wipe products be highly homogeneous. Thus, the components should be homogeneously distributed in the composition so as to provide consistent application of the composition to, or distribution of the composition in, wipe substrates, the skin, or other surfaces. It is also desirable for the composition to rapidly de-emulsify upon application to the skin, and to resist re-emulsification after such application.

The residue left by a wipe should also have several properties. The residue should protect the skin against irritants accompanying body waste, yet should not significantly reduce transepidermal moisture loss, i.e., the skin should be allowed to breathe even in the presence of the residue (thus, the residue is non-occlusive). Occlusive barrier agents tend to cause excess hydration of the skin, which renders the skin more susceptible to irritation or infection. Moreover, it is desirable for the residue to provide easier cleansing of the perineal region.

In addition, it is often desirable that the residue and the wipe provide a favorable esthetic, particularly tactile, perception to the user of the wipe (the user of the wipe may be a wearer of an incontinence article or a care-giver to such wearer). For example, the residue and the wipe should not be excessively greasy, oily, or tacky and should provide an impression of softness or silkiness. The residue should have a sufficiently low coefficient of friction to minimize the risk of skin abrasion or red-marking, and to improve the spreadability of other protective barrier agents that may be applied. The wipe should provide an impression of sufficient wetness and should feel soft and non-irritating to the user.

Finally, the composition used in the disposable wipe should not negatively impact the physical properties of the nonwoven substrate so as to excessively reduce its utility for the intended application. In addition, the composition should inhibit the growth of a broad range of bacteria, fungi and other microorganisms.

While the art has provided several compositions having various levels of utility in personal cleansing or treatment for the prevention of perineal dermatitis, the art has not provided the desirable characteristics of such compositions in the manner or to the extent of the present invention.

It is therefore an object of the present invention to provide a composition that is useful for personal cleansing and for reducing the risk of perineal dermatitis. More particularly, it is an object to provide such compositions that are highly homogeneous and which rapidly de-emulsify upon application to skin and that do not tend to re-emulsify, so as to ensure a substantially uniform, yet non-occlusive, layer of substantive protective barrier agent on the skin. It is a further object of the present invention to provide such compositions which are esthetically pleasing to the user. Another object of the invention is to provide such compositions that have a coefficient of friction that is sufficiently low so as to minimize the risk of skin abrasion or red-marking, to provide easier subsequent cleansing of the skin, and to improve the spreadability of other protective barrier agents that may be applied.

It is another object of the invention to provide a method of making such compositions.

Yet another object of the invention is to provide wipe products containing the composition, more particularly a wipe product that provides effective cleansing and that also leaves a substantive, highly protective residue on the skin. Another object of the invention is to provide a wipe product that is soft and non-irritating to the user.

SUMMARY OF THE INVENTION

The present invention is directed to compositions for cleaning and leaving a protective residue on the skin of a person, the composition being especially useful for reducing the risk of perineal dermatitis. The compositions contain water, a silicone oil and an emulsifier. Preferred compositions also include a water-soluble polyol, a pH-adjusting agent, an anti-microbial agent and/or a chelating agent. The components are combined to provide a stable, tactilely pleasant, non-irritating lotion that can rapidly de-emulsify upon application to the skin and remain de-emulsified to leave on the skin a substantially uniform protective layer of the silicone oil. The silicone oil tends to reduce the risk of perineal dermatitis, red-marking, and skin abrasion and tends to aid in the removal of body waste and in the application of other topical agents.

In preferred embodiments the silicone oil includes dimethicone and the emulsifier is a polymeric emulsifier, more preferably a carboxylic acid polymeric emulsifier, most preferably comprising an acrylates/$C_{10}$–$C_{30}$ alkyl acrylate crosspolymer. The preferred anti-microbial agent includes a mixture of 1,3-bis(hydroxymethyl)-5,5-dimethylhydantoin and 3-iodo-2propynyl butyl carbamate.

The present invention also relates to the use of the compositions in combination with a substrate to effect cleaning, treating, or other uses. In a preferred embodiment, the composition is pre-combined with the substrate to form a wipe product, e.g., disposable wipe products, to be used for such purposes at a later time. In a preferred embodiment, the wipe product includes a nonwoven substrate impregnated with the composition. The preferred wipe products tend to be resistant to a wide range of microorganisms, such that the wipes have a good storage life. The wipe products also tend to be soft relative to wipe products that do not contain silicone oil, or wipe products that do not incorporate silicone oil substantially throughout the wipe product.

The invention also relates to methods of making the compositions. A preferred method involves adding the pH-adjusting agent at the end of the process of making the composition, or before an optional dilution step. The preferred method also uses a relatively low shear process of forming an emulsion of the silicone in the composition. The preferred method tends to provide highly homogeneous compositions that rapidly de-emulsify upon application to skin and that tend to remain de-emulsified so as to leave on the skin a substantially uniform layer of silicone oil.

DESCRIPTION OF PREFERRED EMBODIMENTS

The compositions of the present invention are emulsions containing water, a protective barrier agent that includes a silicone oil, and an emulsifier. In preferred embodiments, the composition also contains at least one additional component selected from water-soluble polyols, pH-adjusting agents, anti-microbial agents and chelating agents. Additional ingredients, e.g., fragrance; skin soothing aids, moisteners, humectants and emollients; powders and the like may also be included in the composition.

The water serves as a medium for carrying the protective barrier agent to the skin in an esthetically pleasant manner and at a suitable viscosity. In addition, the water aids in wetting of the substrate of wipe products incorporating the composition. The water may be deionized or tap water. Tap water is economically preferred. However, it may be preferred to use deionized water to minimize interference with emulsification due to trace metals and other trace compounds that may be found in tap water, or to otherwise provide control in manufacturing of the composition. The compositions of the present invention generally contain at least about 80%, more preferably at least about 85%, most preferably at least about 90% water, and up to about 99.5% water, by weight of the composition. Particularly preferred compositions contain from about 91% to about 99.5% water, by weight of the composition.

The silicone oil is the primary protective barrier agent in the composition. The silicone tends to provide a protective barrier against body waste irritants while at the same time allowing normal transepidermal moisture loss such that the skin is not excessively hydrated. In addition, the silicone oil provides emolliency, lubricates the skin surface and tends to release soil to thereby facilitate skin cleaning. The silicone oil tends to impart less tack than other emollients that have been used in personal cleansing compositions, e.g., animal oils such as lanolin or petroleum based oils such as petrolatum and mineral oil. The silicone also imparts a feeling of silkiness, smoothness and softness to the user's skin, and tends to soften wipe products incorporating the composition.

Silicone oils that are useful herein are those that can be stably emulsified. Preferred silicone oils are those that impart a tactile impression of softness and smoothness, and which do not impart an excessive tactile perception of greasiness, oiliness, or coating, when incorporated into the composition. Non-volatile silicone oils are preferred over volatile silicone oils. Non-volatile silicones tend to provide wipe products that remain stable when exposed to the environment, tend to provide a lasting tactile impression, and tend to form a stable oil layer on the skin. Mixtures of silicones can be used. For example, volatile silicones may be used in combination with non-volatile silicones to impart desired esthetic properties, as long as the composition contains sufficient non-volatile silicone to provide a skin barrier layer that is effective for a given application.

Exemplary silicone oils that are suitable for used herein include dimethicone (alternatively referred to as linear polydimethylsiloxane polymer, dimethyl silicone), substituted linear dimethicones, cyclomethicone, dimethiconol, trimethylsiloxysilicate, and mixtures thereof. Such silicones are commercially available, for example, from the Dow Corning Company of Midland, Mich. under the trade names Dow Corning 200 fluid (dimethicone), Dow Corning 1401 fluid (cyclomethicone and dimethiconol), Dow Corning 593 fluid (dimethicone and trimethylsiloxysilicate), and Dow Corning 2503 fluid (stearyl dimethicone). These and other silicone oils that may be suitable for use herein are described in the technical brochure numbered 24-414C-93 and entitled "Shaping Solutions for Personal Care," Dow Corning Corporation, Midland, Mich. 1993.

In a preferred embodiment, the silicone oil is a linear dimethicone or mixture of linear dimethicones, more preferably a linear dimethicone or mixture thereof having a viscosity in the range of 50 to 1,000 centistokes (i.e., "cs"). Exemplary dimethicones are available from Dow Corning under the trade names Dow Corning 200 Fluid. In a particularly preferred embodiment, the silicone oil is the Dow Corning 200 Fluid having a viscosity of about 350 centistokes. It has been found that this silicone oil provides a protective barrier without imparting an excessively greasy, oily, or tacky feeling to the composition when incorporated in the particularly preferred amounts.

The silicone oil is employed in an amount of at least about 0.5% and up to about 10%, by weight of the composition, with an amount of at least about 0.5% and less than about 5% being preferred. Particularly preferred compositions contain from about 0.5% to less than about 3%, more preferably 0.5% to about 2.5%, most preferably from about 1% to about 2.5% silicone oil, based on the weight of the composition. Compositions containing the latter silicone content tend to provide a particularly suitable balance of skin protection and esthetic properties. The composition also includes an emulsifier such as are known in the art of forming oil-in-water emulsions. The emulsifier is preferably a polymeric emulsifier. The polymeric emulsifier is capable of primary emulsification of the composition, and of rapidly de-emulsifying upon application of the composition to the skin to form a silicone oil film on the skin. In addition, the polymeric emulsifier does not tend to re-emulsify once the composition is applied to the skin. This is particularly important where the composition is to be used to clean or treat the perineal region, in which region repeated insults of urine can occur between changes of the diaper or other incontinence device. Since the composition does not re-emulsify to a significant extent, the silicone oil tends to remain on the skin in the form of a protective barrier layer, rather than being washed away by urine or other body fluids.

The emulsifier is employed in an amount effective to emulsify the silicone oil and other non-water-soluble oils that may be present in the composition (hereinafter alternatively referred to as "an effective amount"), typically an amount ranging from about 0.05% to about 1.0%, preferably from about 0.05% to about 0.5%, based on the weight of the composition. Particularly preferred compositions of the present invention contain from about 0.1% to about 0.5%, more preferably from about 0.1% to about 0.3%, most preferably from about 0.1 to about 0.2% emulsifier, based on the weight of the composition. Mixtures of emulsifiers may be used.

Polymeric emulsifiers that are suitable for use herein include, but are not limited to carboxylic acid polymers which are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. Combinations of these two types of polymers are also useful herein.

The first type of preferred carboxylic acid polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The monomers are preferably selected from the group consisting of acrylic acid, methacrylic acid, ethacrylic acid, and mixtures thereof, with acrylic acid being most preferred.

The second type of preferred carboxylic acid polymer is a crosslinked copolymer having (i) a first monomer selected from the group consisting of an acrylic acid monomer or derivative thereof (as just described in the previous paragraph), a shod chain alcohol (i.e. $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and (ii) a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl —CN —COOH and mixtures thereof). The acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The shod chain alcohol acrylate ester monomer or derivative thereof is preferably selected from the group consisting of $C_{1-4}$ alcohol acrylate esters $C_{1-4}$ alcohol methacrylate esters $C_{1-4}$ alcohol esters, and mixtures thereof with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of the first and second types of preferred carboxylic acid polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof.

The carboxylic acid polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein in their entirety. See also, CTFA International Cosmetic Ingredient Dictionary, fourth edition, 1991, pp. 12 and 80; which are also incorporated herein by reference in their entirety.

Examples of commercially available carboxylic acid polymers of the first type useful herein include the carbomers, which are homopolymers of acrylic acid crosslinked with allyl ethers of sucrose or pentaerythritol. The carbomers are available as the Carbopol® 900 series from the B. F. Goodrich Company of Cleveland, Ohio. Examples of commercially available carboxylic acid copolymers of the second type useful herein include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerythritol. These copolymers are known as acrylates/C10–30 alkyl acrylate crosspolymers and are commercially available as Carbopol® 1342, Pemulen® TR-1, and Pemulen® TR-2, from B. F. Goodrich. In other words, examples of carboxylic acid polymeric emulsifiers useful herein are those selected from the group consisting of carbomers, acrylates/C10–C30 alkyl acrylate crosspolymers, and mixtures thereof.

The acrylates/C10–C30 alkyl acrylate crosspolymers are particularly preferred for use in the present invention. These emulsifiers can be generally described as hydrophobically modified hydrophilic polymers that tend to both emulsify oils in water and to stabilize the finished emulsion. They are predominantly high molecular weight polyacrylic acid based polymers having a small lipophilic portion and a large hydrophilic portion. These crosspolymers tend to provide improved oil in water emulsification relative to other known polymeric emulsifiers, and may offer the additional advantage of obviating the need for a buffer.

The Pemulen® emulsifiers are most preferred in the compositions of the present invention. The Pemulen® emulsifiers have a relatively high level of hydrophobicity and thus tend to form emulsions wherein the silicone oil droplets are highly stabilized against coalescence and creaming. In addition, the Pemulen® emulsifiers, and particularly Pemulen® TR-2, tend to enable lower viscosities. A relatively low viscosity is preferred for the personal cleansing wipe products of the present invention to ensure sufficient impregnation of the wipe product, for cleansing efficiency, and to provide a positive tactile impression. At the same time, compositions containing the Pemulen® emulsifiers tend to remain substantially uniformly distributed in the wipe product, i.e., settling of the composition does not occur to a significant extent. The Pemulen® emulsifiers and their use in personal care compositions are described in more detail in the technical brochure, "Introducing the New, Universal Pemulen® Polymeric Emulsifiers," B. F. Goodrich Company, April 1994, and in "Pemulen® Polymeric Emulsifiers: What They Are, How They Work," R. Dodwell, R. Lockhead, W. Hemmeker, both incorporated herein by reference.

Additional emulsifiers that are useful herein are disclosed in the above referenced U.S. Pat. No. 5,043,155 issued to Puchalski et al., which is incorporated herein by reference in its entirety.

In preferred embodiments, the composition also contains one or more components selected from water-soluble polyols, pH-adjusting agents, anti-microbial agents and chelating agents.

Water-soluble (which includes water-miscible) polyols are polyols that are able to uniformly dissolve or disperse in water. The water-soluble polyol may serve several purposes in the composition. For example, the polyol may function as a skin moistener, humectant, or emollient. The polyol may additionally or alternatively potentiate the anti-bacterial agent. The polyol may be used as a solvent for one or more components of the composition.

Water-soluble polyols that are suitable for use herein include water-soluble alkylene polyols and water-soluble analogs of such polyols. Water-soluble analogs of these polyols include water-soluble esters of alkylene polyols. Non-limiting examples of water-soluble polyols suitable for use herein include ethylene glycol, propylene glycol, butylene glycol, diethylene glycols, triethylene glycols, other water-soluble polyethylene glycols, water-soluble polypropylene glycols, hexylene glycol, glycerol, polyoxyethylene sorbitol, 1,2,4- butane triol, 1,2,6-hexane triol, sorbitol and mixtures thereof. Propylene glycol is an economically preferred polyol. Butylene glycol and hexylene glycol, and particularly hexylene glycol, tend to potentiate the antimicrobial agent and are therefore preferred to provide a higher level of protection against the growth of microorganisms. Therefore, these glycols, and particularly hexylene glycol, are preferred for providing greater storage stability to the composition and wipe products containing the composition. These glycols may be particularly preferred where the wipes are formed from a porous substrate, e.g., a nonwoven.

The water-soluble polyol is employed in an amount effective to provide the desired function or functions, e.g., as a skin moistener, humectant and/or emollient, as a solvent for other components of the composition, or to potentiate the anti-bacterial agent (herein alternatively referred to as "an effective amount"). Typically, the water-soluble polyol will be used in an amount of from about 0.5 to about 3%, preferably from about 0.5 to about 2%, more preferably from about 0.5 to about 1%, based on the weight of the composition. Mixtures of such agents may be used.

It is generally desired in personal cleansing or treating compositions to adjust the pH of the composition to that or near that of skin. Therefore, the pH will typically be adjusted as may be necessary to provide the composition with a pH of from 4 to 7, more preferably from 4.5 to 6.5. The pH can be adjusted by adding one or more pH-adjusting agents in an amount effective to provide such pH values (herein alternatively referred to as "an effective amount"). Agents that may be used to adjust the pH of the compositions herein include organic and inorganic acids and bases.

For the preferred compositions of the present invention, which employ a carboxylic acid polymeric emulsifier, the composition in the absence of a pH-adjusting agent tends to be more acidic than desired. Therefore, a basic pH-adjusting agent will typically be used to bring the composition to the desired pH. Basic pH-adjusting agents include organic amine bases, preferably amines that are relatively non-irritating and which have a relatively low equivalent weight, for example, triethanolamine, trimethylamine, tromethamine, aminomethyl propanol and tetrahydroxy ethylene diamine. Higher grade versions (i.e., at least 99% pure) of organic amine bases are preferred. Inorganic bases, including alkali metal salts such as NaOH, can also be used. The organic amines will typically be preferred since they have a lower risk of irritation, and their titration is more readily controlled, relative to inorganic bases. Other pH-adjusting agents are described in the above referenced U.S. Pat. No. 5,043,155.

The amount of the pH-adjusting agent that is employed depends on the equivalent weight of the pH-adjusting agent and the desired pH. Typically, the pH-adjusting agent is used in an amount of from about 0.01 to about 0.5 weight % of the composition. Preferred compositions of the present invention include from about 0.05 to about 0.2 weight %, typically about 0.1 to about 0.2 weight % pH-adjusting agent.

Anti-microbial agents may function in one or more ways to improve the shelf life of the composition and products incorporating the composition. For example, the anti-microbial may be a preservative, an anti-bacterial agent, an anti-fungal agent, or a combination thereof. The anti-microbial agent is used as may be required in an amount which is effective to provide a suitable shelf life (storage stability, i.e., microorganisms do not grow to a significant extent) (herein alternatively referred to as "an effective amount"). Useful products will typically have a shelf life of at least 1 year under storage conditions of about 75° F. and 50% Relative Humidity (measured in accordance with United States Pharmacopeia test entitled "Microbial Test, Antimicrobial Preservative —Effectiveness"). The anti-microbial agent is typically used in an amount of from 0.05% to about 0.5% based on the weight of the composition. Preferred compositions of the present invention employ from about 0.1 to about 0.3 weight % anti-microbial agent. One or more anti-microbial agents may be employed.

The anti-microbial agent is preferably substantially water-soluble and insoluble in the silicone oil. Anti-microbial agent wherein include, but are not herein include, but are not limited to, those described in the above referenced and incorporated U.S. Pat. No. 5,043,155 issued to Puchalski et al., and in U.S. Pat. No. 4,844,891 issued to Rosen et al. on Jul. 4, 1989, incorporated herein by reference. A preferred anti-microbial agent is available from Lonza, Inc. of Fairlawn, N.J. under the trade name Glydant Plus®. Glydant Plus® comprises a mixture of 1,3-bis(hydroxymethyl)-5,5-dimethylhydantoin (i.e., DMDMH) and 3-iodo-2-propynyl butyl carbamate (the mixture may also comprise a minor amount of hydroxymethyl-5,5-dimethylhydantoin (i.e., DMH)). It has been found that the Glydant Plus® is highly effective in preventing the growth of a wide variety of microbes, and is advantageously efficacious against the growth of fungi. This tends to be particularly important where the wipe product contains a porous substrate, for example, nonwoven substrates. The Glydant Plus® tends to provide wipe products having exceptional storage stability under a variety of storage conditions, including storage at or below the temperature of freezing. Alternatively preferred anti-microbial agents are described in the above-referenced and incorporated U.S. Pat. No. 4,844,891.

The composition preferably contains one or more chelating agents. The chelating agent tends to bind metals (e.g., calcium ions, magnesium ions) that may be present in the composition so as to enhance the efficiency of the emulsifier and the anti-microbial agent. Thus, the chelating agent may be considered to provide a level of anti-microbial activity to function, for example, as a preservative. The chelating agent may be used in an amount that is effective to bind the aforementioned metals (hereinafter alternatively referred to as an "effective amount"), typically an amount ranging from about 0.01% to about 0.2 weight % of the composition. Particularly preferred compositions include from about 0.05% to about 0.2%, more preferably from about 0.05% to about 0.15% chelating agent, based on the weight of the composition. Chelating agents and their use in personal cleansing compositions are well known in the art. Exemplary chelating agents are disclosed in the above referenced U.S. Pat. No. 5,043,155 and include disodium EDTA, trisodium EDTA, and tetrasodium EDTA.

The composition may optionally include other ingredients, e.g., fragrance; skin soothing aids such as panthenol, bisabolol, green tea extract, kola extract, ichthammol, stearyl glycyrrhetinate, ammonium glycyrrhetinate, Vitamin E (tocopherol or tocopherol acetate), and aloe; skin moisteners, humectants, or emollients other than those previously described; powders and the like.

The compositions of the present invention will contain from about 84 to about 99.5 weight % water and about 0.5 up to about 10 weight % silicone oil. Preferred compositions contain from about 91 to about 99.5 weight % water and about 0.5 to less than 3 weight % silicone oil, more preferably about 0.5 to about 2.5 weight % silicone oil; most preferably about 1 to about 2.5 weight % silicone oil. Such compositions will contain an effective amount of emulsifier as previously described. The compositions may also contain one or more agents selected from antimicrobial agents, water-soluble polyols, pH-adjusting agents, and chelating agents as previously described. These agents may be used in an effective amount as previously described.

Thus, compositions of the present invention may contain from about 84 to about 99.5 weight % water, from about 0.5 to about 10 weight % silicone oil, and from about 0.05 to about 1 weight % emulsifier. The composition preferably contains from about 91 to about 99.5 weight % water, from about 0.05 to about 1 weight % emulsifier, and from about 0.5 to less than 3 weight % silicone oil, more preferably about 0.5 to about 2.5 weight % silicone oil, most preferably about 1 to about 2.5 weight % silicone oil.

Particularly preferred compositions will contain an anti-microbial agent, a water-soluble polyol, a pH-adjusting agent, and a chelating agent in the amounts previously described. Preferred compositions of this type contain from about 91 to about 99 weight % water, from about 0.5 to less than 3 weight % silicone oil, from about 0.05 to about 1 weight % emulsifier, from about 0.05 to about 0.5 weight % anti-microbial agent, from about 0.5 to about 3 weight% water-soluble polyol, from about 0.01 to about 0.5 pH-adjusting agent, and from about 0.01 to about 0.2 weight % chelating agent. Compositions of this type more preferably contain from about 0.5 to about 2.5, most preferably from about 1 to about 2.5, weight % silicone, the amounts of the other non-aqueous ingredients and water being within the ranges stated in this paragraph and balancing the composition to 100 weight %. The water content of these latter compositions may range from about 92 to about 99% and, respectively, from about 92 to about 98.5%.

Exemplary preferred compositions of the present invention thus include:

(A) from about 92 to about 99 weight % water, from about 0.5 to less than 3 weight % silicone oil, from about 0.1 to about 0.5 weight % emulsifier, from about 0.05 to about 0.5 weight % anti-microbial agent, from about 0.5 to about 3 weight % water-soluble polyol, from about 0.01 to about 0.5 pH-adjusting agent, and from about 0.01 to about 0.2 weight % chelating agent;

(B) from about 94.5 to about 99 weight % water, from about 0.5 to about 2.5 weight % silicone oil, from about 0.1 to about 0.3 weight % emulsifier, from about 0.1 to about 0.3 weight % anti-microbial agent, from about 0.5 to about 2 weight % water-soluble polyol, from about 0.05 to about 0.2 pH-adjusting agent, and from about 0.05 to about 0.2 weight % chelating agent; and (C) from about 95 to about 98.5 weight % water, from about 1 to 2.5 weight % silicone oil, from about 0.1 to about 0.2 weight % emulsifier, from about 0.1 to about 0.3 weight % anti-microbial agent, from about 0.5 to about I weight% water-soluble polyol, from about 0.1 tO about 0.2 pH-adjusting agent, and from about 0.05 to about 0.15 weight % chelating agent.

In the foregoing compositions, the emulsifier is preferably a polymeric emulsifier, more preferably a carboxylic acid polymeric emulsifier, most preferably an acrylates/$C_{10}$–$C_{30}$ alkyl acrylate/cross polymeric emulsifier. A particularly preferred emulsifier is Pemulen® TR-2. The preferred silicone is dimethicone, more preferably dimethicone having a viscosity of from 50 to 1000 centistokes, most preferably a viscosity of 350 centistokes. The preferred anti-microbial agent comprises a mixture of 1,3-bis(hydroxymethyl)-5,5-dimethylhydantoin and 3-iodo-2-propynyl butyl carbamate such as previously described.

The compositions may be prepared by oil-in-water emulsion techniques such as are known or become known in the art. In general, the process involves the steps of preparing a mixture of the ingredients of the composition and subjecting the mixture to conditions to cause the formation of a homogeneous and stable oil-in-water emulsion (a suspension of the silicone oil in the water and water-soluble materials is formed). Homogeneity is indicated by a composition which is substantially smooth, lump-free and uniform in appearance. A stable emulsion remains homogeneous over a given period which is determined by the required shelf life of the composition.

The mixture may be formed in one step by addition and mixing of each of the ingredients. Alternatively, less than all of the ingredients may be pre-combined for subsequent combination with other ingredients or other pre-combined ingredients to form the mixture. For example, the antimicrobial agent may be pre-mixed with a portion of the water, water-soluble polyol, or a mixture thereof.

In a preferred embodiment, at least a portion of the water, the emulsifier, the silicone oil, and the optional water-soluble polyol, anti-microbial agent and chelating agent are first combined and subjected to conditions to form the emulsion. The pH-adjusting agent is then added and mixed into the emulsion. Where the resultant emulsion has been prepared with less than the finally desired level of water, the emulsion may thereafter be diluted to form the composition of the invention. When this process is employed, the composition tends to be particularly homogeneous. Such compositions tend to be more uniformly distributed on and/or absorbed by a substrate to be used in the wipe products described herein. In addition, the film of silicone oil that is subsequently formed on the skin tends to be more uniform to thereby provide a more effective protective barrier layer. In addition, this method tends to reduce energy needs for manufacturing the composition.

The mixture may contain each of the ingredients in the total amounts intended. Alternatively, the mixture may contain less than the total of each ingredient, typically less than the entire amount of water, such that a concentrated emulsion is formed. The concentrate will typically be designed to provide both a volume that is preferred for storage and/or shipping, and a workable viscosity. For example, a 5-fold concentrate may be formed. The concentrated emulsion may then be diluted by adding the balance of the ingredients to form the composition of the present invention. A suitable method of forming an emulsion concentrate is described in the above-referenced U.S. Pat. No. 5,043,155. Although the use of a concentrated emulsion technique may be economically preferred, it has been found that such a technique is not required to obtain the compositions of the present invention.

Equipment suitable for forming the mixtures and emulsion may be selected from those known in the art or which become known in the art. For example, suitable apparatii include dual propeller blade mixers. A turbine mixer and an in-line homogenizer using tandem rotor-stators, such as described in the above-referenced U.S. Pat. No. 5,043,155, may also be used. A single shaft motor equipped with two propeller blades has been found to be suitable for preparing the compositions of the present invention. In a preferred configuration, the shaft extends substantially through the depth of the mixing vessel and has a first blade that is positioned as near the bottom of the vessel as is possible and a second shaft positioned within approximately the lower half, preferably the lower fourth, of the vessel, and more preferably within about 1 foot of the first blade. The first blade preferably has a diameter approaching that of the vessel diameter, more preferably as near to that of the vessel as possible, while the second blade may be the same size or substantially smaller. The mixer is suitably rated to drive a free shaft at a speed of from 1,000 rpm to about 15,000 rpm. Preferably, the motor is rated to drive a free shaft at a speed of from about 1000 to at least about 6000 rpm.

To form the emulsion, the mixture is typically mixed for a period of from about 5 to 60 minutes, with the motor speed set to drive a free shaft at a rate of from about 1,000 rpm to about 15,000 rpm, preferably about 1000 rpm to about 6000 rpm. In a particularly preferred embodiment, the mixture is mixed for a period of from about 5 to 30 minutes, with the motor speed set to drive a free shaft at a rate of from about 1000 rpm to about 3000 rpm. As will be understood by the skilled artisan, care should be taken to avoid subjecting the mixture to excessive shear, which may interfere with emulsification.

The resultant emulsion containing the ingredients in their total amounts has a preferred viscosity at room temperature (i.e., 20°–25° C.) in the range of from about 10 to about 200 centipoise (i.e., cps), more preferably from about 15 to about 150 cps, most preferably from about 20 to about 100 cps. The viscosity can be determined using a Brookfield RVT viscometer equipped with a #1 spindle at a speed of 20 rpm according to the readily available and commonly used procedures for the Brookfield viscometer or an equivalent apparatus and method. The emulsion tends to remain stable for a period in excess of one year at room temperature, or one month at 45° C. Instability is indicated by a significant variation, typically a significant decrease, in viscosity. Instability is also indicated by the appearance of layers in the depth of the composition, when viewed from a horizontal perspective in a transparent container with the naked eye.

The compositions of the present invention are particularly useful for personal cleansing and/or skin treating applications. The compositions can be applied directly to the skin, for example, by spraying, dripping, smoothing, rubbing, massaging and the like. Additionally or alternatively, the compositions can be applied with the use of a suitable applicator comprising a substrate material for holding the composition. Non-limiting examples of substrate materials are sponges, foams, nonwovens, films and the like. Thus, the compositions of the present invention are particularly suitable for use in combination with a substrate to effect personal cleansing, skin treating, or other personal care uses. In a preferred embodiment, the composition is pre-combined with the substrate to form a wipe product, e.g., disposable wipe products, to be used for such purposes at a later time. As used herein, "wipe product" means a substrate and a composition of the present invention which are pre-combined for later use. Disposable wipe products are those which are intended to be discarded after a single use (i.e., the original wipe product in its whole is not intended to be laundered or otherwise restored or reused as a wipe product, although certain materials or all of the wipe product may be recycled, reused, or composted). The compositions and wipe products are well-suited for use in cleaning and/or treating the perineal area of infants or other incontinent individuals (e.g., for use as infant wipes or incontinent adult wipes). However, it is to be understood that the compositions and wipe products of the present invention are useful in other applications, including but not limited to facial and hand cleansing and/or treating.

Suitable wipe substrates include nonwovens, films, foams, sponges, and the like. Preferred wipe substrates comprise a porous material which is capable of holding the composition within the pores of the substrate. Therefore, preferred substrates include nonwovens, foams, sponges and the like. For infant and incontinent adult wipe products, the substrate will preferably be a nonwoven. Nonwoven substrates used for the wipe product can be formed of cellulosic fibrous materials, synthetic polymeric fibrous materials, or a combination thereof (e.g., conform). For example, the nonwoven may contain from about 1% to 99% by weight cellulosic fiber and, respectively, from about 99% to 1% by weight synthetic polymeric fibers. Non-limiting examples of such materials include paper tissue, paper toweling, and nonwovens formed from rayon, polyolefins, polyester fibrous material or a combination of such materials with cellulosic fibers. The nonwovens may be air-laid, wet-laid, spun-laid, meltblown, or carded. The nonwoven may include one or more layers of fibrous material; e.g. a laminate of fibrous material. The separate layers may be formed of similar or dissimilar materials. The nonwoven may be treated, for example, to join the fibers of the nonwoven or to enhance the strength of the nonwoven. Such treatment may involve hydroentanglement, thermal bonding, or treatment with a binder.

Cellulosic nonwovens, particularly nonwovens wherein the fibrous material consists essentially of cellulosic products, are economically and environmentally preferred. Cellulosic nonwovens that are especially suitable for use in the present invention are described in U.S. Pat. No. 3,905,863 issued to Ayers on Sep. 16, 1975; U.S. Pat. No. 3,974,025 issued to Ayers on Aug. 10, 1976; and U.S. Pat. No. 4,191,609 issued to Trokhan on Mar. 4, 1980. Each of these references are incorporated herein by reference in their entirety.

Techniques for combining wipe substrates with a cleansing or treating composition, and for their packaging are well known in the art and are applicable to the present invention. In general, the wipe substrate is combined with the composition by one or more techniques involving coating, immersing, dipping, spraying, extruding, and the like. In general, the wipes are combined with an amount of the composition sufficient to provide good effective cleansing. It is often important to employ a loading that provides an acceptable tactile impression (e.g., sufficient but not excessive wetness, not excessively greasy or oily). Thus, the wipe substrates are typically combined with the composition in an amount of from about 2 to about 8 times, preferably about 3 to about 5 times the dry weight of the substrate. For example, a suitable incontinent adult wipe for use in cleansing the perineal area, which contains a cellulosic nonwoven, may contain the composition in an amount of about 3 times the dry weight of the nonwoven.

The following non-limiting examples are representative of the present invention.

EXAMPLES (a) Preparation of a composition according to the present invention:

An emulsion containing about 96.4% water, 2% silicone oil, 0.15% carboxylic acid polymeric emulsifier, 1% water soluble alkylene polyol, 0.1% chelating agent, 0.2% antimicrobial agent, 0.15% organic base pH-adjusting agent, and fragrance is prepared in the following manner.

A standard size, 55 gallon, covered cylindrical drum fitted with a single shaft having dual propeller blades, driven by a motor rated at 1750 rpm, is used to prepare the emulsion. The shaft extends substantially through the depth of the drum (about 4 feet) and has a first blade that is positioned near the bottom of the drum and a second shaft positioned about 1 foot above the first blade. The first blade has a diameter approaching that of the drum diameter (about 2 feet), and the second blade has a diameter of about 1 foot.

The drum is charged with 40.48 gallons of tap water. Agitation of the water is begun by operating the motor at its maximum rated speed. Agitation at this speed is continued throughout the entire process.

0.52 lbs. Pemulen® TR-2 is added slowly, to allow mixing of the emulsifier with the water sufficient to disperse or avoid the formation of lumps of the emulsifier. The following components are then added in the order stated: 0.35 lbs tetrasodium EDTA; 3.49 lbs propylene glycol; 6.97 lbs dimethicone (Dow Corning 200 Fluid, 350 cs); 0.70 lbs Glydant Plus®; 0.01 lbs of fragrance. Each of the foregoing ingredients are individually mixed into the water until they are well blended into the resultant mixture, typically by agitating for a period of about 1 minute between addition of the individual ingredients, and for a period of about 5–10 minutes once all the ingredients are added to the vessel.

0.52 lbs triethanolamine is then added and agitation is continued for a period of about 15–20 minutes, or until the mixture is well blended. The pH of the composition is about 6.5. Lower or higher pH compositions can be prepared in a similar manner by adding more or less triethanolamine, respectively. For example, a composition having a pH of from 5–6 can be prepared by adding a lower level of triethanolamine. The resultant emulsion has a viscosity of about 120 cps (Brookfield LVT, #3 spindle, 30 rpm, 60° F., measured upon stabilization of viscometer reading after approximately 15 seconds of spindle rotation).

(b) Preparation of a disposable wipe product containing composition according to the invention:

A wipe composed of a two-ply cellulose substrate of 100% NSK fiber, having a Basis Weight of 26 lbs per ply and a Caliper of 20 mils per ply, are laminated together under pressure with an adhesive, and rolled into a continuous web roll. Suitable adhesives have a wet strength that is sufficient for the plies to remain substantially bonded in use. The web roll is slit to achieve the desired finished wipe width (e.g., 11.5" in the unfolded configuration), and z-folded so that the machine direction edges overlap about 0.5'.

The resultant slitted and folded webs are then impregnated with the composition prepared in (a) by passing the individual webs over the top of individual manifolds having holes through which the composition is pumped under pressure onto the moving web. The composition is pumped so as to provide a loading of about 15.5 grams of composition per finished wipe.

Following impregnation, the webs cut to the desired finished wipe length (e.g., about 8.5").

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe product comprising a substrate and a dilute emulsion composition, said emulsion composition comprising:

(a) at least about 90% by weight water;

(b) about 0.5% to less than 3%, by weight silicone oil; and (c) a polymeric emulsifier in an amount effective to emulsify said silicone oil in said water, wherein said polymeric emulsifier is a carboxylic acid polymeric emulsifier.

2. The product of claim wherein said composition contains from about 0.5% to about 2.5%, by weight, of said silicone oil.

3. The product of claim 2 wherein said composition contains from about 1% to about 2.5%, by weight, of said silicone oil.

4. The product of claim 1 wherein said polymeric emulsifier is a carboxylic acid polymeric emulsifier.

5. The product of claim 1 wherein said carboxylic acid polymeric emulsifier is an acrylates/C10–C30 alkyl acrylate crosspolymer.

6. The product of claim 1 wherein said silicone oil is a dimethicone polymer having a viscosity of from about 50 to about 1000 centistokes.

7. The product of claim 6 wherein said dimethicone polymer has a viscosity of about 350 centistokes.

8. The product of claim 1 further comprising an agent selected from the group consisting of anti-microbial agents, pH-adjusting agents, chelating agents, water-soluble polyols, and mixtures thereof.

9. The product of claim 8 wherein said anti-microbial agents is a mixture of 1,3-bis(hydroxymethyl)-5,5-dimethylhydantoin and 3-iodo-2-propynyl butyl carbamate.

10. The product of claim 8 wherein said pH-adjusting agents is an organic basic amine.

11. The product of claim 8 wherein said water-soluble polyols are selected from the group consisting of water-soluble alkylene polyols, water-soluble esters of alkylene polyols, and mixtures thereof.

12. The product of claim 11 wherein said water-soluble alkylene polyols is a $C_3$–$C_8$ alkylene glycol.

13. A wipe product comprising a substrate and an emulsion composition, said composition comprising:
(a) about 90 to about 99.5 weight % water;
(b) about 0.5 to less than 3 weight % silicone oil;
(c) a carboxylic acid polymeric emulsifier comprising an acrylates/C10–C30 alkyl acrylate crosspolymer in an amount effective to emulsify said oil in said water; and
(d) an effective amount of an anti-microbial agent comprising a
mixture of 1,3-bis(hydroxymethyl)-5,5-dimethylhydantoin and 3-iodo-2-propynyl butyl carbamate.

14. The product of claim 13 wherein said composition comprises from about 0.5% to about 2.5%, by weight, of said silicone oil.

15. The product of claim 14 wherein said composition comprises from about 1% to about 2.5%, by weight, of said silicone oil.

16. The product of claim 13 wherein said silicone oil comprises a dimethicone polymer having a viscosity of from about 50 to about 1000 centistokes.

17. The product of claim 13 wherein said composition additionally comprises an effective amount of an agent selected from the group consisting of basic pH-adjusting agents, chelating agents, and mixtures thereof.

18. The product of claim 18 wherein said composition additionally comprises an effective amount of a water-soluble polyol selected from the group consisting of water-soluble alkylene polyols, water-soluble esters of alkylene polyols, and mixtures thereof.

19. The product of claim 18 wherein said composition comprises:
(a) about 91 to about 99 weight % of said water;
(b) about 0.5 to less than 3 weight % of said silicone oil;
(c) about 0.05 to about 1 weight % of said polymeric emulsifier;
(d) about 0.5 to about 3 weight % of said water-soluble polyol;
(e) about 0.05 to about 0.5 weight % of said anti-microbial agent;
(f) about 0.01 to about 0.2 weight % of said chelating agent, and
(g) about 0.01 to about 0.5 weight % of said basic pH-adjusting agent.

20. The product of claim 19 wherein said composition comprises about 0.5 to about 2.5 weight % of said silicone oil.

21. The product of claim 21 wherein said composition comprises about 1 to about 2.5 weight % of said silicone oil.

22. The product of claim 1 wherein said substrate is a nonwoven comprising cellulosic fibers.

23. The product of claim 1 wherein the product comprises said composition in an amount of from about 2 to about 8 times the dry weight of said substrate.

24. An emulsion composition useful for cleansing or treating the skin of a person, the composition comprising:
(a) at least about 90 weight % water;
(b) about 0.5 to less than 3 weight % of a silicone oil;
(c) a carboxylic acid polymeric emulsifier comprising an acrylates/C10–C30 alkyl acrylate crosspolymer in an amount effective to emulsify said oil in said water; and
(d) an effective amount of an anti-microbial agent comprising a mixture of 1,3-bis(hydroxymethyl)-5,5-dimethylhydantoin and 3-iodo-2-propynyl butyl carbamate.

25. The composition of claim 24 additionally comprising:
(e) an effective amount of a water-soluble polyol selected from the group consisting of water-soluble alkylene polyols, water-soluble esters of alkylene polyols, and mixtures thereof;
(f) an effective amount of a chelating agent, and
(g) an effective amount of a basic pH-adjusting agent.

26. The composition of claim 15 wherein the composition comprises:
(a) about 91 to about 99 weight % of said water;
(b) about 0.5 to less than 3 weight % of said silicone oil;
(c) about 0.05 to about 1 weight % of said polymeric emulsifier;
(e) about 0.05 to about 0.5 weight % of said anti-microbial agent;
(d) about 0.5 to about 3 weight % of said water-soluble polyol;
(f) about 0.01 to about 0.2 weight % of said chelating agent, and
(g) about 0.01 to about 0.5 weight % of said basic pH-adjusting agent.

* * * * *